United States Patent [19]

Graham et al.

[11] Patent Number: 5,919,676
[45] Date of Patent: Jul. 6, 1999

[54] ADENOVIRAL VECTOR SYSTEM COMPRISING CRE-LOXP RECOMBINATION

[75] Inventors: Frank L. Graham; Martina Anton, both of Hamilton; Michael A. Rudnicki, Dundas, all of Canada

[73] Assignee: AdVec, Inc., Hamilton, Canada

[21] Appl. No.: 08/473,168

[22] Filed: Jun. 7, 1995

Related U.S. Application Data

[63] Continuation-in-part of application No. 08/250,885, May 31, 1994, abandoned, which is a continuation-in-part of application No. 08/080,727, Jun. 24, 1993, abandoned.

[51] Int. Cl.[6] .............................. C12N 15/00; C12N 5/00
[52] U.S. Cl. .................................. 435/172.3; 435/320.1; 435/325
[58] Field of Search ........................ 514/44; 435/320.1, 435/172.3, 325; 424/93.21

[56] References Cited

U.S. PATENT DOCUMENTS

| 4,510,245 | 4/1985 | Cousens et al. . |
| 4,797,368 | 1/1989 | Carter et al. . |
| 4,920,209 | 4/1990 | Davis et al. . |
| 4,920,211 | 4/1990 | Tibbetts et al. . |

FOREIGN PATENT DOCUMENTS

| WO 93/19092 | 9/1939 | WIPO . |
| WO 93/06223 | 4/1993 | WIPO . |
| WO 93/19191 | 9/1993 | WIPO . |
| WO 94/08026 | 4/1994 | WIPO . |

OTHER PUBLICATIONS

Orkin et al. Report and Recomendations . . . Gene Therapy. NIHPress. Dec. 7, 1995. p. 1–40.
Miller et al. FASEB. vol. 9:190–199, Feb. 1995.
Marshall. Science.369:1050–1055, Aug. 1995.
Culver et al. TIG. 10(5):174–178, May 1994.
Hodgson. Exp Opin Ther. Patents. 5(5):459–468, May 1994.
Neuwett et al Behavioral and Brain Sciences. 18:1–9 (1995).
Wolf Current Opinion in Neurobiology. 3:743–748 (1993).
McGrory et al Virology, 163:614–617 (1988).
Graham et al. Methods in Molecular Biology 7:109–128 (1991).
Kilby et al. Trends Genet. 9 413–421 (1993).
Yang et al. Proc Natl. Acad. Sci. USA 91:4407–4411 (May 1994).
Anton, M., and F. L. Graham, 1995, Site–specific recombination mediated by an adenovirus vector expressing the Cre recombinase protein: a molecular switch for control of gene expression, J. Virol. 69: 4600–4606.
Araki, K., J. Araki, J. I. Miyazaki, and P. Vassali, 1995, Site-specific recombination of a transgene in fertilized eggs by transient expression of Cre recombinase. Proc. Nat'l. Acad. Sci. USA 92: 160–164.
Bett, A. J., L. Prevec, and F. L. Graham, 1993, Packaging capacity and stability of human adenovirus type 5 vectors. J. Virol. 67: 5911–5921.

Bett, A. J., W. Haddara, L. Prev, and F. L. Graham, 1994, An efficient and flexible system for construction of adenivorus vectors with insertions or deletions in early region 1 and 3. Proc. Nat'l. Acad. Sci. USA 91:8802–8806.
Crystal, R. G., N. G. McElvaney, M. A. Rosenfeld, C. S. Chu, A. Mastrangeli, J. G. Hay, S. L. Brody, H. A. Jaffe, N. T. Eissa, and C. Danel. 1994. Administration of an adenivorus containing the human CFTR cDNA to the respiratory tract of individuals with cystic fibrosis, Nature Genetics 8: 42–51.
DiSanto, J. P., W. Mueller, D. Guy–Grand, A. Fischer, and K. Rajewsky, 1995, Lymphoid development in mice with a targeted deletion of the interleukin 2 receptor chain, Proc. Nat'l. Acad. Sci. USA 92: 377–381.
Gage, P.J., B. Sauer, M. Levin and J. C. Glorioso. 1992. A cell–free recombination system for site–specific integration of multigenic shuttle plasmids into the herpes simplex virus type 1 genome. J. Virol. 66: 5509–5515.
Graham, F. L. and L. Prevec. 1991. Manipulation of adenovirus vectors. In Murray E.J. (ed.), Methods in Molecular Biology. The Humana Press Inc. Clifton, N.J. vol. 7 (Gene Transfer and Expression Protocols): 109–128.
Graham F. L. and L. Prevec. 1992. Adenovirus–based expression vectors and recombinant vaccines. in: Vaccines; New Approaches in Immunological Problems., ed. Ellis, R.W. Butterworth–Heinemann, Boston, MA: 363–390.
Graham F. L., J. Smiley, W. C. Russel and R. Naim. 1977. Characteristics of a human cell line transformed by DNA from human adenovirus type 5., J. Gen. Virol. 36: 59–72.
Gu, H., J. D. Marth, P.C. Orban, H. Mossmann and K. Rajewsky. 1994. Deletion of a DNA polymerase B gene segment in T cells using cell type–specific gene targeting. Science 265: 103–106.
Kilby, N. J., M. R. Snaith, and J. A. H. Murray. 1993. Site–specific recombinases: tools for genome engineering. Trends Genet. 9: 413–421.
Metzger, D., J. Clifford, H. Chiba and P. Chambon. 1995. Conditional site–specific recombination in mammalian cells using a ligand–dependent chimeric Cre protein. Proc. Nat'l. Acad. Sci. USA 92: 6991–6995.
Pichel, J. G., Lakso, and H. Westphal. 1993. Timing of SV40 oncogene activation by site–specific recombination determines subsequent tumor progression during murine lens development. Oncogene 8: 3333–3342.
Sauer, B. 1994. Site–specific recombination: developments and applications. Cur. Opin. Biotech. 5: 521–527.
Sauer, B. and N. Henderson. 1989. Cre–stimulated recombination of loxP–containing DNA sequences placed into the mammalian genome. Nucl. Acids Res. 17: 147–161.

(List continued on next page.)

*Primary Examiner*—Deborah Crouch
*Attorney, Agent, or Firm*—Gerard H. Bencen, Esq.; Gerard H. Bencen, P.A.

[57] ABSTRACT

This invention provides a method for making adenovirus cloning vectors which contain a recombinase target site that is useful for the insertion of selected foreign proteins.

6 Claims, 5 Drawing Sheets

OTHER PUBLICATIONS

Sauer, B., and N. Henderson. 1990. Targeted insertion of exogenous DNA into the eukaryotic genome by the Cre recombinase. The New Biologist 2: 441–449.

Sauer, B., M. Whealy, A. Robbins and L. Enquist. 1987. Site–specific insertion of DNA into a pseudorabies virus vector. Proc. Nat'l. Adac. Sci. USA 84: 9108–9112.

Smith A. J. H., M. A. DeSousa, B. Kwabi–Addo, A. Heppel–Parton, H. Impey, and P. Rabbits. 1995. A site–directed chromosomal translocation induced in embryonic stem cells by Cre–loxP recombination. Nature Genetics 9: 376–385.

Rabbits. 1995. A site–directed chromosomal translocation induced in embryonic stem cells by Cre–loxP recombination. Nature genetics 9: 376–385.

Sternberg, N., B. Sauer, R. Hoess, and K. Abremski. 1986. Bacteriophase P1 cre gene and its regulatory region; Evidence for multiple promotors and for regulation by DNA methylation., J. Mol. Biol. 187: 197–212.

Van Deursen, J., M. Fornerod, B. Van Rees, and G. Grosveld. 1995. Cre–mediated site specific translocation between non–homologous mouse chromosomes. Proc. Nat'l. Acad. Sci. USA 92: 7376–7380.

Mittal, S.K., McDermott, M.R., Johnson, D.C., Prevec, L. and F. L. Graham. 1993. Monitoring foreign gene expression by a human adenovirus–based vector using the firefly luciferase gene as a reporter, Virus Research, 28: 67–90.

Hanke, T., Frank L. Graham, Kenneth L. Rosenthal and David C. Johnson. 1991. Identification of an immunodominant cytotoxic t–lymphocyte recognition site in glycoprotein B of herpes simplex virus by using recombinant adenovirus vectors and synthetic peptides. 1991. J. of Virology, 65: 1177–1186.

Graham, F.L., 1987. Growth of 293 cells in suspension culture. J. Gen. Virol. 68: 937–940.

Quantin, B., Leslie D. Pericaudet, Shahragim Tajbakhsh and Jean–Louis Mandel. 1992. Adenovirus as an expression vector in muscle cells in vivo. Proc. Nat'l. Acad. Scie. 89: 2581–2584.

Bett, A.J., Wael Haddara, Ludvik Prevec and Frank L. Graham, 1994. Proc. Nat'l. Acad. Sci. 91: 8802–8806.

Rosenfeld, M.A. et al., 1992. In vivo transfer of the human cystic fibrosis transmembrane conductance regulator gene to the airway epithelium, Cell. 68: 143–155.

W. J. McGrory, D. S. Baulista and F. L. Graham. 1998. A simple technique for the resue of early region 1 mutations into infectious human adenovirus type 5, Virology 163: 614–617.

Wang, P., Anton, F. L. Graham and S. Bacchetti. High Frequency recombination between loxP sites in human chromosomes mediated by an adeniovorus vector expressing Cre recombinase. Submitted for publication.

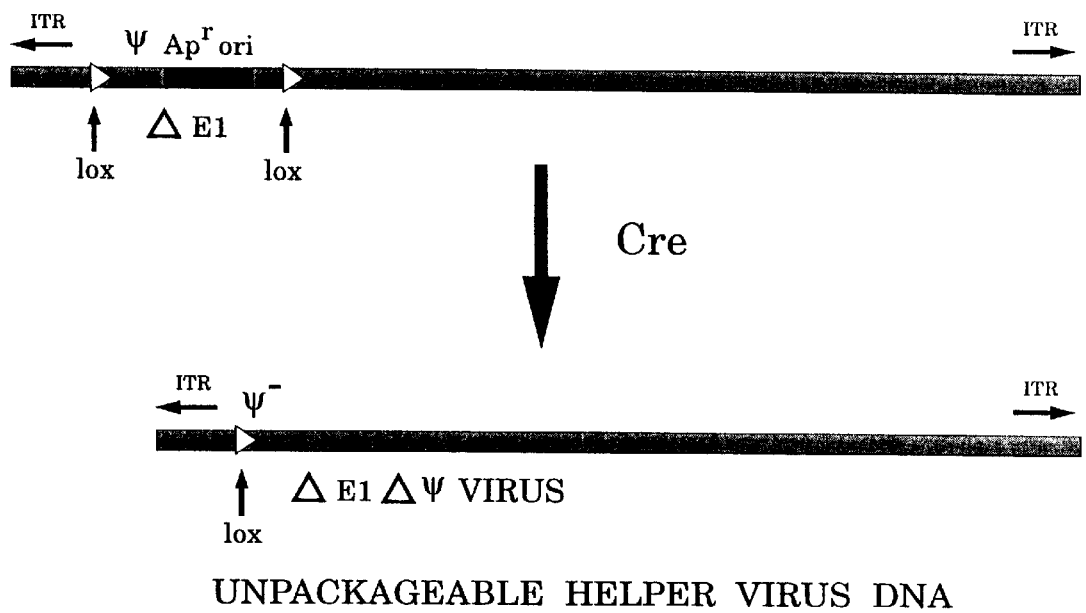
UNPACKAGEABLE HELPER VIRUS DNA
+
FIG. I

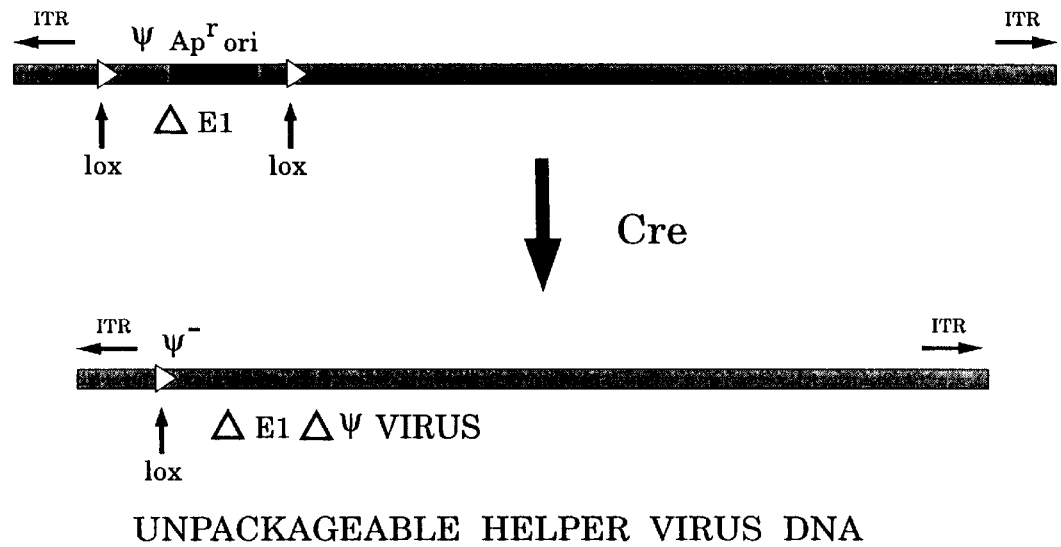
UNPACKAGEABLE HELPER VIRUS DNA
PROVIDES ESSENTIAL VIRAL FUNCTION
IN TRANS (HELPER FUNCTIONS) FOR:
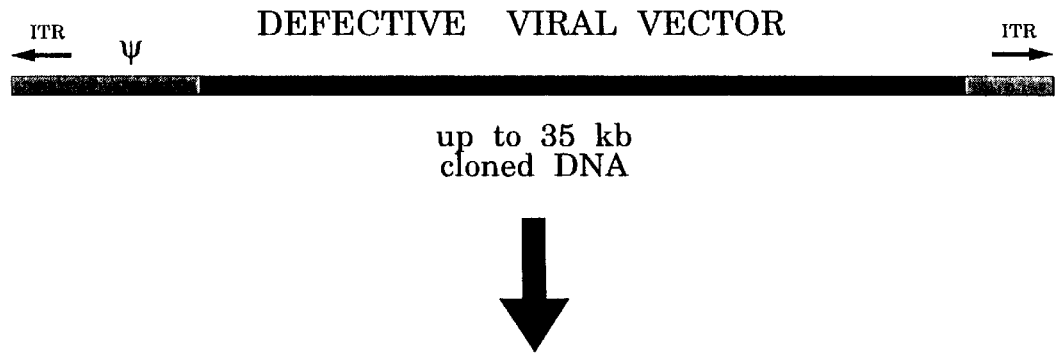
REPLICATION OF BOTH VECTOR & HELPER DNA
PACKAGING OF VECTOR DNA ONLY
FIG. 2

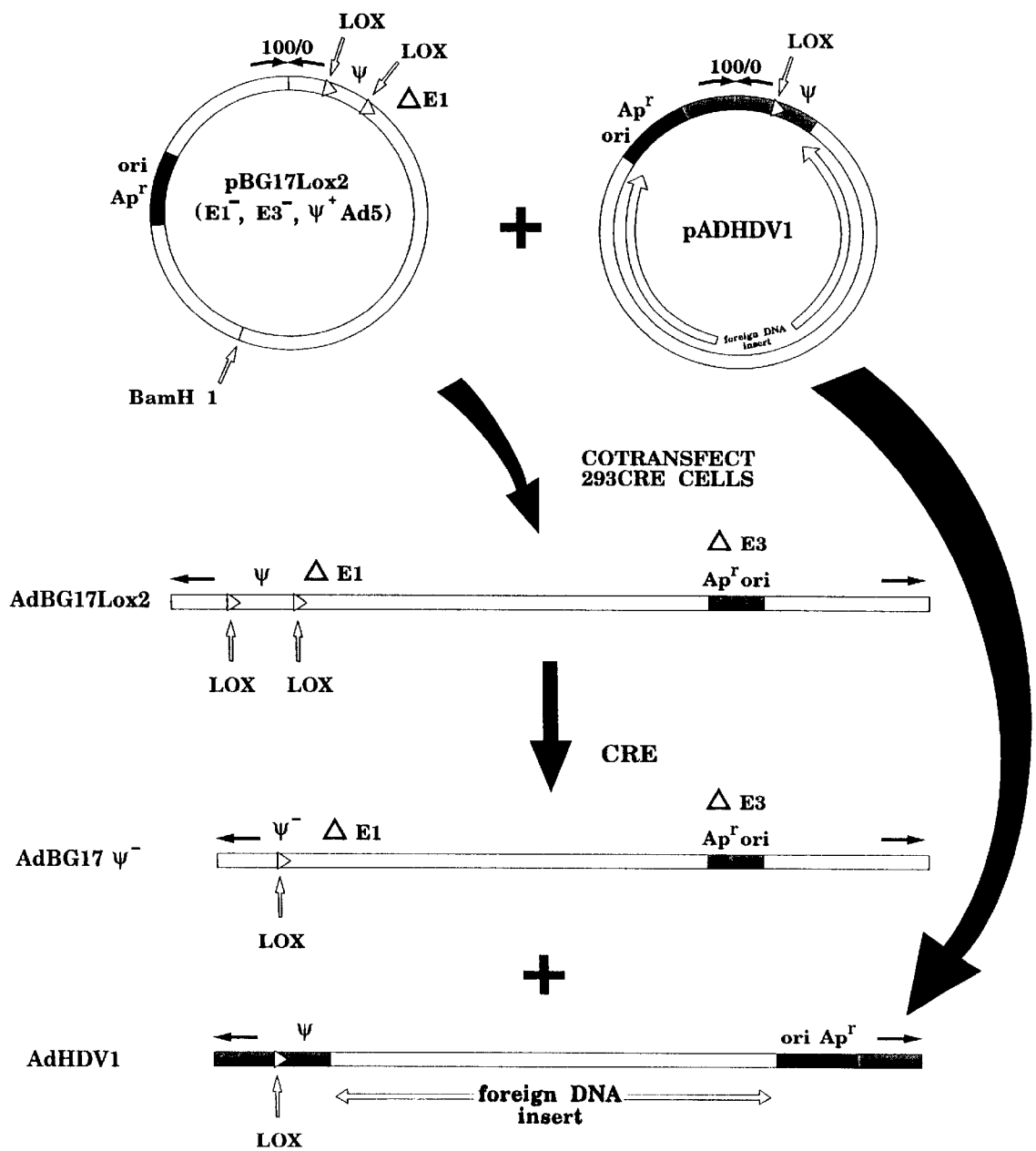
F I G. 5

ADENOVIRAL VECTOR SYSTEM COMPRISING CRE-LOXP RECOMBINATION

This application is a continuation-in-part of application Ser. No. 08/250,885 filed on May 31, 1994 now abandoned which is itself a continuation-in-part of application Ser. No. 08/080,727 filed Jun. 24, 1993 now abandoned from which priority is also claimed. Both of these applications are hereby incorporated by reference.

FIELD OF THE INVENTION

The present invention relates to adenovirus vectors that have increased utility for gene transfer into mammalian cells. The vector systems described have increased capacity for insertion of foreign DNA and improved safety.

BACKGROUND OF THE INVENTION

Parent application Ser. No. 08/250,885, filed on May 31, 1994, and its parent application Ser. No. 08/080,727 disclose and claim a genus of adenovirus (Ad)-derived cell expression vectors having excellent potential as live recombinant vaccines and as transducing vectors for gene therapy. In the human Ad genome, early region 1 (E1), E3, and a site upstream of E4 have been utilized as sites for introducing foreign DNA sequences to generate adenovirus recombinants. In the absence of compensating deletions in E1 or E3 a maximum of about 2 kb can be inserted into the Ad genome to generate viable virus progeny. The E1 region is not required for viral replication in complementing 293 cells and up to 3.2 kb can be deleted in this region to generate conditional helper independent vectors with a capacity of 5.0–5.2 kb. In the E3 region, which is not required for viral replication in cultured cells, deletions of various sizes have been utilized to generate nonconditional helper independent vectors with a capacity of up to 4.5–4.7 kb.

The maximum capacity for inserts of foreign DNA in currently available helper independent Ad vectors such as those described in the parent application is approximately 8 kb. This limited capacity arises from the use of Ad vectors which have deletions of E1 and E3 sequences and from the fact that most other regions of the viral genome must be retained in order that the viral vector may be propagated without the need for a helper virus.

Besides this limited capacity for insert DNA, previous vectors retain most of the viral genome, expression of viral genes in transduced cells or in inoculated animals, including humans, can result in toxic or other untoward effects. In addition, previous viral vectors can recombine with Ad sequences present in cells used for propagation of the vectors or with Ad sequences that may be present in inoculated animals. Therefore, it is the objective of this invention to provide Ad cloning vectors from which all or most viral genes have been removed and which will have increased safety and capacity for larger insertions compared to currently available vectors.

SUMMARY OF THE INVENTION

It is the goal of this invention to provide a simple and useful system by which high capacity Ad5 cloning vectors may be developed. As demonstrated in concurrently filed application Ser. No.08/486,549 filed Jun. 7, 1995, entitled "Adenoviruses for Control of Gene Expression") provision of Cre recombinase in Ad infected cells can catalyze excision or rearrangement of viral DNA sequences that contain the target sites (loxP) for Cre mediated site specific recombination. In the present invention, use is made of this knowledge to construct Ad5 genomes in which the viral DNA packaging signals can be excised from the viral genome by action of Cre. Said excision of said packaging signal results in a viral DNA that is unable to package into virion particles. Such a viral DNA, though unable to package into virions, may encode viral functions that provide complementing functions for replication of a second, viral "vector", that lacks substantial portions of the viral genome so that in coinfected cells though both helper and vector DNAs may replicate, only the vector DNA can be packaged into virions.

One embodiment of the present invention provides a bacterial plasmid comprising a circularized modified human adenovirus type 5 (Ad5) genome that contains sequences that can be recognized and acted upon by a site specific recombinase known as Cre. Said bacterial plasmid is able to generate infectious Ad5 carrying the modified sequences including the sequences that can be recognized by Cre. The structure of the modified sequences in the bacterial plasmid and in viruses generated from said plasmid is such that recombination catalyzed by Cre will result in excision of sequences, known as the packaging signal, near the left end of the Ad5 genome, that are required for packaging of Ad5 DNA into infectious virion particles. Optionally, certain regions of the plasmid and resulting viruses may be deleted, such as sequences from E1 or E3 that can be omitted from the viral genome without preventing the viral genome from replicating in such cells as may be permissive for replication of said viral genome in the form of infectious virus.

A second embodiment of the invention provides a bacterial plasmid comprising approximately 340 base pairs from the left end of the Ad5 genome, including the left end terminal repeat sequences of said genome and the packaging signal sequences thereof and the right terminal repeat sequences of the Ad5 genome. The left end of the left terminal repeat sequence is joined in "head to tail" configuration with the right end of the right terminal repeat. Between approximately nucleotide 340 near the left end of the genome and approximately nucleotide 35,800 near the right end of the genome, are substituted restriction enzyme sites suitable for insertion of foreign DNA sequences.

A third embodiment of the invention provides a mammalian cell line, such as a human cell line, that provides the Cre recombinase enzyme. Alternatively, Cre may be provided by an Ad5 derived vector that expresses the Cre protein in suitable cells.

Other embodiments of the present invention include Ad genome constructs, known as "vectors", containing substantial deletions of viral DNA sequences that are substituted with large insertions of foreign DNA 20–35 kb in length. Such genomes are unable to replicate as viruses in the absence of viral products provided by a second virus, hereafter called a "helper" virus.

One specific embodiment of the invention is a helper virus that can be designed, propagated, and used in such a way that when employed to support replication of a second virus, the vector, from which substantial portions of the viral genome have been deleted and substituted with foreign DNA, said "helper" virus DNA is unable to be packaged into infectious virions.

BRIEF DESCRIPTION OF FIGURES

FIG. 1 is a diagrammatic representation of Cre mediated excision of DNA from a viral vector in which the packaging signal is flanked by lox P sites.

FIG. 2 is a diagrammatic representation of a method to generate helper dependent viral vectors using Cre mediated excision of the packaging signal to prevent packaging of the helper virus DNA.

FIG. 5 is a diagrammatic representation of a means to obtain coreplicating helper and helper dependent viruses by cotransfection of 293 Cre cells.

DETAILED DESCRIPTION OF THE INVENTION

Figure 3:
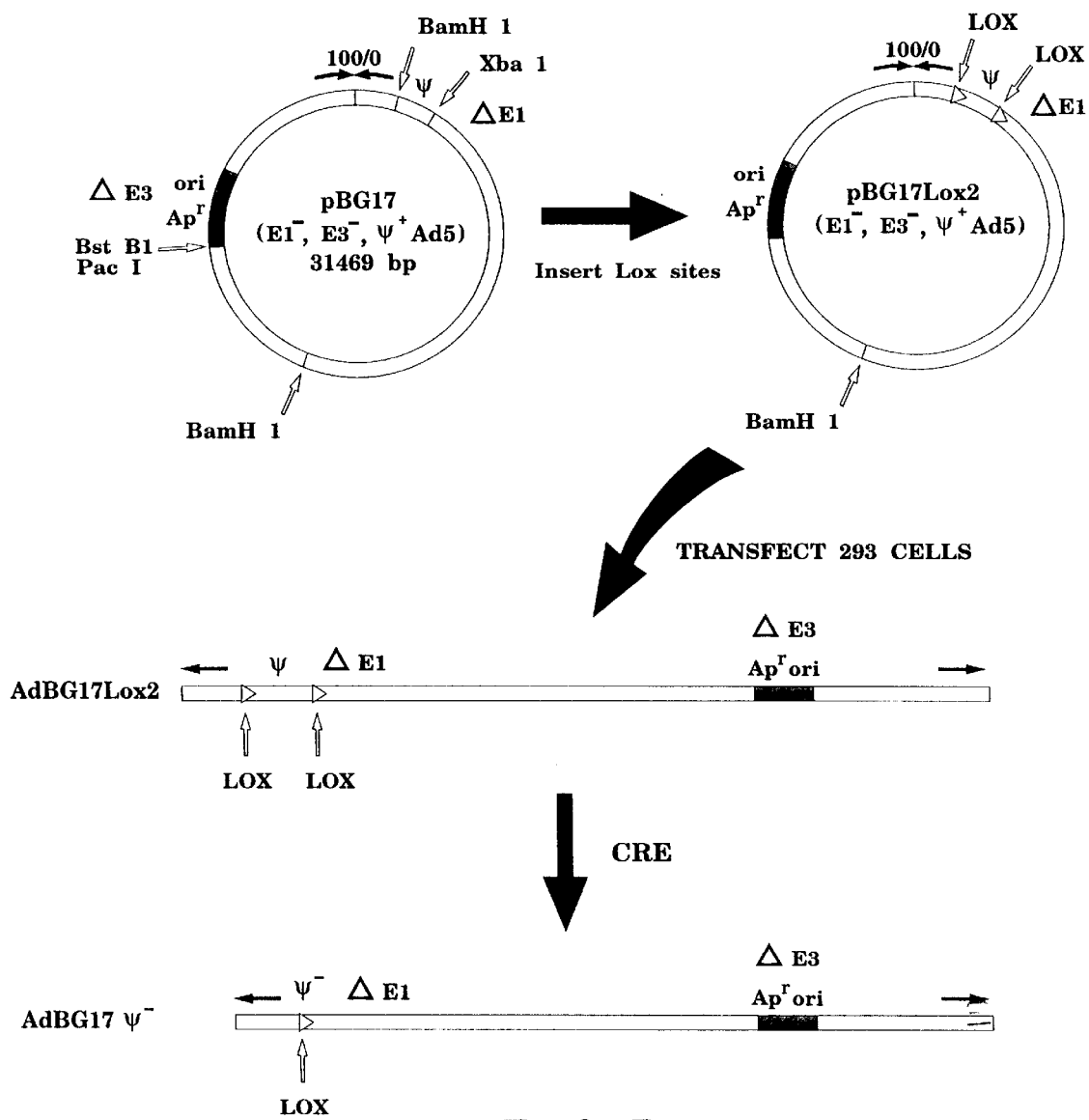
FIG. 3 is a diagrammatic representation of a plasmid derived from pBHG10 into which lox P sequences have been introduced at positions flanking the packaging signal.

Any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives can be made and will hybridize to one another and to DNA and RNA, and the use of such analogues and derivatives is also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by a nucleic acid, but further encompasses nucleic acids encoded by other nucleic acids (e.g., non-coding and regulatory RNAs such as tRNA, sNRPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labelled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics* 4: 560–569 (1989); Landren et al., *Science* 241: 1077–1080 (1988); Nickerson et al., *Proc. Natl. Acad. Sci.* 87: 8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., *PCR Methods and Applications* 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by references, and in Ausubel et al., *Current Protocols in Molecular Biology,* John Wiley and Sons, Baltimore, Md. (1989), which is also hereby incorporated by reference. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind the recombinantly produced fragment. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic oligonucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

*E. coli* is one prokaryotic host useful particularly for cloning DNA sequences of the present invention. Other microbial hosts suitable for use include bacilli, such as *Bacillus subtilus,* and other enterobacteriaceae, such as Salmonella, Serratia, and various Pseudomonas species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. Saccharomyces is a suitable host, with suitable vectors having expression control sequences, such as promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

The method lends itself readily to the formulation of test kits for use in diagnosis. Such a kit comprises a carrier compartmentalized to receive in close confinement one or more containers wherein a first container contains suitably labeled DNA probes. Other containers contain reagents useful in the localization of the labeled probes, such as enzyme substrates. Still other containers contain restriction enzymes, buffers etc., together with instructions for use.

The recombinant Ad vectors described herein are significantly different from previously described constructs. They combine the use of vectors having deletions of all or most of the viral genes with helper viruses that are designed so that, when used in coinfections with vector viruses, said helper viruses are able to complement the growth of the vectors but are unable to package their viral DNA into infectious virions. Thus vector viruses can be prepared substantially free of helper virus.

For viral DNA replication and packaging of viral DNA into virion particles, only three regions of the viral DNA are known to be required in cis. These are the left inverted terminal repeat , or ITR, (bp 1 to approximately 103) the packaging signals (approximately 194 to 358 bp) (Hearing and Shenk, 1983, Cell 33: 695–703; Grable and Hearing 1992, J. Virol. 64: 2047–2056) and the right ITR. All other regions of the viral genome appear to be required only to produce viral products that act in trans to allow viral replication and production of infectious viruses. Thus if all essential viral proteins and RNA could be provided by a helper virus, a vector could be designed and constructed that could have most of the viral DNA deleted save for those sequences mentioned above that are required in cis for viral DNA replication and packaging. A problem with helper dependent vectors has been that preparations of such vectors are invariably contaminated with helper virus and it is technically very difficult to separate the helper from the vector. In the main embodiments of the present invention the helper virus is designed to have two lox P sites near the left end of the genome, one inserted at approximately 189 bp from the extreme left end of the viral DNA, and the second, in parallel orientation with the first lox P, situated rightward of the packaging signals, ie rightward of bp 358 (diagrammed in FIG. 1). This virus will be able to replicate in cells that are normally permissive for growth of Ad5. However, in cells that express the Cre recombinase, or in the presence of a second virus that expresses Cre recombinase, excision of sequences between the lox P sites of the helper virus DNA will remove the packaging signal, and the resulting viral DNA will fail to package into infectious viral particles. Therefore, in cells coinfected with said helper and with a second virus, a vector from whose genome have been deleted all or most of the viral DNA sequences that are normally required for expression of viral products necessary in trans for viral replication, both vector and helper viral genomes will replicate but only the vector DNA that retains the packaging signal will be packaged into virions (FIG. 2).

Figure 4:
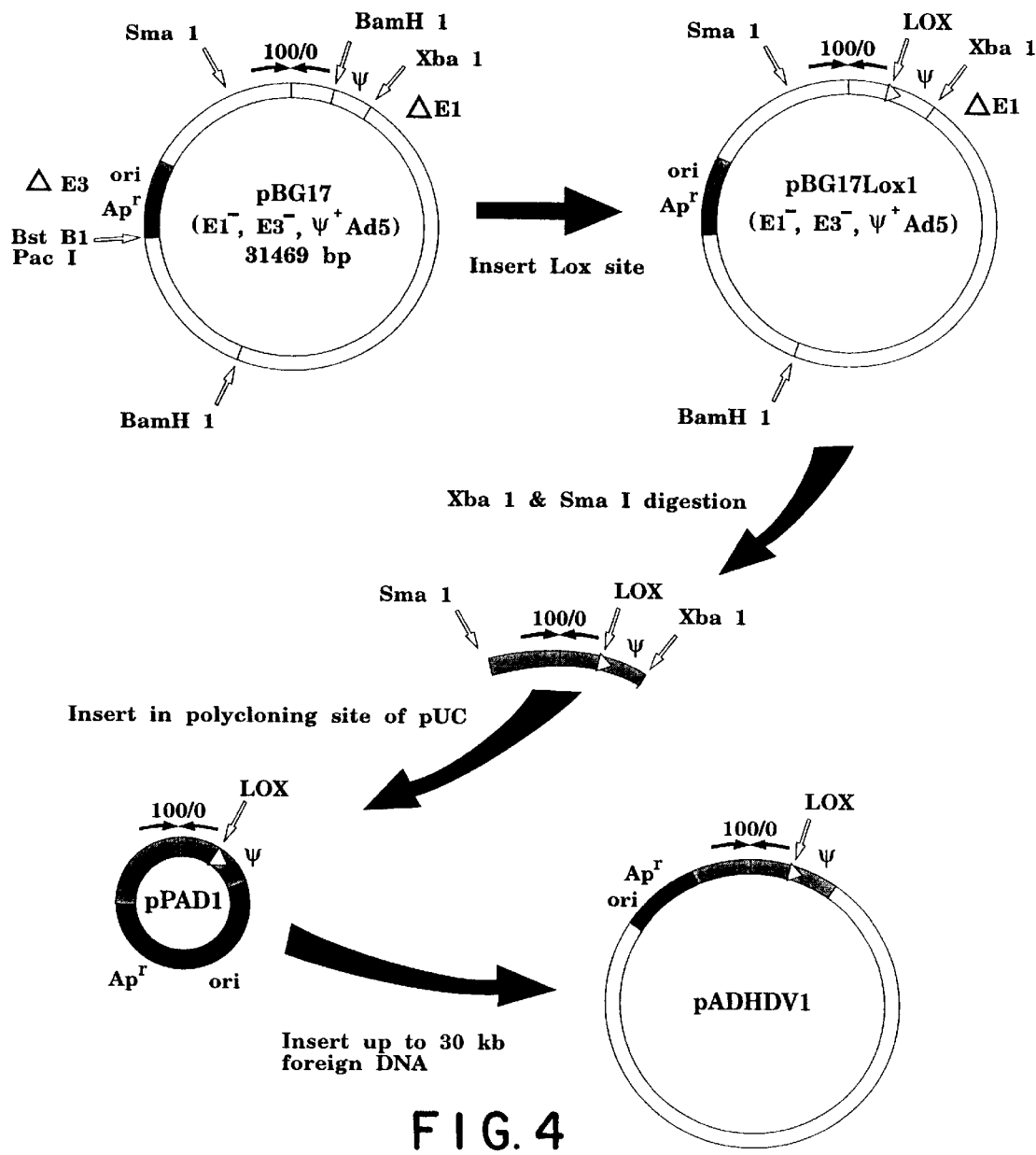
FIG. 4 is a diagrammatic representation of a plasmid derived from pBHG10 from which most of the viral DNA has been deleted save for the left and right ITRs and the packaging signal.

In one embodiment of the invention, the helper virus is derived from a plasmid similar to ones described in the parent application and as illustrated in FIGS. 3 and 4. In these examples, the Ad5 genome is present as a circular molecule containing a bacterial plasmid derived origin of DNA replication (designated "ori") and a bacterial antibiotic resistance coding sequence ("Ap$^r$") conferring to bacteria carrying said molecule resistance to ampicillin. In this example in which said circular form of the Ad5 genome is designated pBG17, viral sequences from regions E1 and E3 have been deleted from the viral genome, but this example is not meant to be limiting since other deletions or no deletions may equally be engineered in the circularized molecule by methods described in the parent application. The molecule designated pBG17 contains Ad5 sequences from bp 19 (left genomic end) to bp 341 with an artificially engineered BamH 1 restriction site inserted between approximately bp 188 and 189 in the Ad 5 sequences which is between the "ITR" and the packaging signal, "ψ", and known not to interfere with viral replication (Bett, A. J., W. Haddara, L. Prevec, and F. L. Graham. 1994, Proc. Natl. Acad. Sci. U.S.A. 91: 8802–8806). Ad 5 sequences present in pBG17 then extend rightward of the packaging signal to approximately bp 341 at which position is located an Xba 1 restriction site followed by Ad 5 sequences from approximately bp 3534 to approximately bp 27864, then sequences comprising 1874 bp of DNA containing the pUC19 origin of replication and ampicillin resistance gene, and finally Ad5 bp 30996 to 35934 (right genomic end). By techniques that are readily employed by a person skilled in the art, lox P sites, which are well defined DNA sequences of about 34 bp, can be introduced into the Ad5 genome at the Bam HI and XbaI sites flanking "ψ". For example synthetic double stranded oligodeoxnucleotides can be readily designed and synthesized such that they contain the lox P sequence recognized by cre and are flanked by single stranded extensions that allow ligation into BamHI or XbaI cleaved DNA. Thus a person skilled in the art can readily obtain the plasmid designated pBG17Lox1 (FIG. 4) having a lox P site introduced into the Bam HI site at nt 188, and subsequently pBG17Lox2 (FIG. 3) having an additional lox P site introduced into the XbaI site of pBG17Lox1. The plasmid pBG17 can be used to generate infectious virus by transfection of 293 cells. Equally, the plasmids pBG17Lox1 or pBG17Lox2, will generate infectious virus (eg. AdBG17Lox2 illustrated in FIG. 3) since insertions of up to 271 bp can be engineered between the ITR and the packaging signal without: interfering with viral replication and packaging of: viral DNA (Hearing et al., Journal of Virology Vol 61, p 2555, 1987). In the presence of Cre enzyme the sequences containing the packaging signal will be excised as a result of intramolecular recombination between the two lox P sites (FIG. 3, bottom) resulting in a viral genome that retains all the sequences necessary for replication but lacks the sequences needed for packaging of DNA into virions. Said genome may serve as a complementing viral genome to support the replication of a second virus, a vector, that lacks all or most of the viral genes necessary for viral replication as diagrammed in FIG. 2. These examples are not meant to be limiting as it will be appreciated that modified viruses similar in DNA structure to that of FIG. 3 can be generated by other means. For example a person skilled in the art could introduce lox P sites into other sites in the plasmids illustrated in FIG. 3 such as the Bst B1 or Pac I sites or into such other locations as might be desirable, or into such other plasmids containing Ad sequences, or other Ad viral genomes as might be desirable. Use of Cre recombinase in this and other examples is not meant to be limiting as a person skilled in the art will readily appreciate that other enzymes capable of catalyzing site specific recombination between DNA sequences recognized by said enzymes could equally be employed in place of the Cre recombinase. An example, not meant to be limiting, of such an enzyme that could be substituted for Cre is the "FLP" recombinase of yeast in combination with its target site (O'Gorman et al. Science 251, 1351, 1991).

Another embodiment of the invention provides human cells, such as 293 cells or other cells that may be deemed suitable in that they support the replication of the viral components of the invention, that express Cre recombinase and that can be transfected with the plasmids described in the previous examples to generate a helper virus from which the packaging signals have been removed through excision mediated by Cre. It will be appreciated by those skilled in the art that the requisite cell lines can be generated by transfecting 293 cells or other cells with a plasmid comprising the coding sequences for Cre under the control of suitable regulatory sequences including a promoter and polyadenylation signal and containing in addition a selectable gene encoding, for example, resistance to G418 or histidinol. A person skilled in the art can readily obtain drug resistant cells that will express the Cre recombinase in addition to the drug resistance gene used for selection.

In another embodiment of the invention, a plasmid consisting of sequences comprising the left ITR, the packaging signal, and the right ITR, and optionally containing additional viral sequences can be readily obtained. An example, which is not meant to be limiting, is illustrated in FIG. 4. In this example, pBG17Lox1 DNA is digested with restriction enzymes XbaI and SmaI which cleave the viral DNA in pBG17Lox1 at sites shown, as well as at other sites in viral DNA. The fragment containing the junction of viral termini (indicated by head to head arrows in FIG. 4) and the lox P site and packaging signal, can be purified and inserted into the polycloning site of a suitable cloning plasmid such as pUC18 or pUC19 to generate the plasmid designated as pPAD1. This example is not meant to be limiting as a person skilled in the art could equally insert said fragment into such other cloning plasmids as might be suitable or desirable. In the example illustrated, pPAD1 can serve as a vector for insertion of foreign DNA up to approximately 30 kb in size at one of the remaining restriction enzyme cloning sites present at the junctions of pUC and Ad5 DNA, to generate a plasmid such as pADHDV1, in which the open segment of pADHDV1 represents foreign DNA of arbitrary origin and sequence composition. The plasmid pADHDV1 contains all the Ad5 sequences needed in cis for viral DNA replication and packaging of viral DNA into virions. Provided that viral functions necessary in trans are supplied by a helper virus, therefore, pADHDV1 will have the potential to replicate as a helper dependent viral DNA molecule that will contain up to 30 kb of foreign DNA flanked by viral DNA sequences from the left and right ends of the viral genome. It may be advantageous to include as part of the foreign DNA inserted in pADHDV1, a DNA sequence capable of providing expression of a readily detectable reporter gene in addition to other sequences, the reporter gene providing a simple means of identifying cells or groups of cells that are infected with the virus ADHDV1 derived from pADHDV1. As an example which is not meant to be limiting, a person skilled in the art could include in pADHDV1, sequences coding for bacterial β-galactosidase, expression of which is readily detectable by exposure of cells to X-gal. Furthermore, in the example shown in FIG. 4, pPAD1 and pADHDV1 contain a single lox P site at Ad5 nt 189, that is at the same site as for one of the lox P insertions in pBG17Lox1&2. Although this example is not meant to be limiting, placement of a lox P site at this position in pPAD1, pADHDV1, and derivatives, may serve to reduce the efficiency of recombination between helper virus and vector during coreplication of the two viruses as illustrated in FIGS. 2 and 5.

In another embodiment of the invention, coreplication of helper virus comprising sequences derived from a plasmid such as pBG17Lox2 and a helper dependent virus comprising sequences derived from a plasmid such as pADHDV1 may be achieved by cotransfection of cells with said plasmids to generate replicating viral genomes. In the example illustrated in FIG. 5, which is not meant to be limiting, AdBG17Lox2 will, in the presence of Cre recombinase, be converted to AdBG17ψ- by excision of the sequences bracketed by lox P sites. The virus AdBG17ψ- will, by virtue of the removal of the packaging signals, be unable to package its genome into virions but will be able to replicate its DNA and provide viral functions necessary in trans for viral replication and thereby provide complementing functions for replication of the helper dependent virus, AdHDV1. Because AdHDV1 retains the packaging signals the DNA of this helper dependent virus will be packaged into virions. The helper dependent virus AdHDV1 may be recovered, and optionally purified and concentrated by isopycnic centrifugation in CsCl gradients to produce helper dependent virus preparations substantially free or totally free of contaminating helper virus.

In another embodiment of the invention, 293 cells or other human cells that do not express Cre may be transfected with a plasmid such as that designated as pBG17Lox2 in FIGS. 3 and 5 to produce a virus such as that designated as AdBG17Lox2. Said virus may replicate in said cells without undergoing excision of sequences bracketed by lox P and can therefore be readily propagated. Coinfection of 293 Cre or equivalent cells with AdBG17Lox2 and AdHDV1 will lead to formation of AdBG17ψ- which will complement; the growth of AdHDV1 resulting in coreplication of both viral genomes but packaging only of AdHDV1 DNA into viral particles.

We claim:

1. An adenovirus vector system for expressing foreign DNA sequences, comprising an isolated cell co-infected with:

a) a helper adenovirus comprising an E1 region where the packaging signals contained within the E1 region are flanked on both sides by lox P recombinase target sites; and b) a helper-dependent adenovirus vector comprising:
   1) a deletion of up to approximately 35,000 bp of the adenovirus genome but retaining sufficient left and right ITR to support viral replication and packaging; and
   2) a fragment or fragments of foreign DNA sequence of up to about 35,000 bp;

and wherein the cell supports replication of the helper adenovirus, and where the cell additionally expresses Cre recombinase.

2. A plasmid for making the helper adenovirus of claim 1, said plasmid comprising an adenovirus genome wherein the E1 region of the adenovirus genome is replaced by a) the packaging signals for the viral genome flanked by lox P sites, b) a bacterial origin of replication and c) an antibiotic resistance gene.

3. A plasmid for making a helper-dependent adenovirus of claim 1, said plasmid comprising an adenovirus genome having up to approximately 35,000 bp deleted, but retaining an adenoviral packaging signal and sufficient right and left ITR to support adenovirus replication, a bacterial origin of replication, an antibiotic resistance gene and a foreign DNA sequence of up to 35,000 bp.

4. The plasmid of claim 3, where in the antibiotic is ampicillin.

5. A method of making a helper adenovirus genome comprising infecting an isolated cell with an adenovirus comprising an E1 region where the packaging signals are flanked on both sides by lox P sites, wherein the cell expresses Cre recombinase, and incubating the infected cells such that the Cre recombinase excises the packaging signals such that the helper adenovirus genome does not package.

6. A method of making a packaged helper-dependent adenovirus vector comprising co-infecting an isolated cell with:

a) a helper adenovirus vector comprising an E1 region where the packaging signals contained within the E1 region are flanked on both sides by lox P recombinase target sites;

b) a helper-dependent adenovirus vector comprising:
   1) a deletion of up to approximately 35,000 bp of the adenovirus genome but retaining an adenoviral packaging signal and sufficient left and right ITR to support viral replication and packaging; and
   2) a fragment or fragments of foreign DNA sequence of about 35,000 bp, wherein the cell supports replication of the helper adenovirus, and where the cell expresses Cre recombinase, and incubating the co-infected cells such that the Cre recombinase catalyzes the removal of the packaging signals from the helper adenovirus vector such that it replicates but does not package, and wherein the helper virus supports replication of the helper-dependent adenovirus vector, and wherein the helper-dependent adenovirus vector is packaged into adenovirus virions.

* * * * *